US010576108B2

(12) United States Patent
Ishii et al.

(10) Patent No.: US 10,576,108 B2
(45) Date of Patent: *Mar. 3, 2020

(54) TAU PROTEIN PRODUCTION ACCELERATOR, AND THERAPEUTIC OR PREVENTIVE AGENT AND THERAPEUTIC OR PREVENTIVE FOOD COMPOSITION FOR DISEASES CAUSED BY TAU PROTEIN DEFICIENCY

(71) Applicant: WELL STONE CO., Miyazaki (JP)

(72) Inventors: Yoichi Ishii, Miyazaki (JP); Takayuki Nemoto, Miyazaki (JP); Takeshi Okamoto, Miyazaki (JP)

(73) Assignee: WELL STONE CO., Miyazaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/513,927

(22) Filed: Jul. 17, 2019

(65) Prior Publication Data

US 2019/0365826 A1    Dec. 5, 2019

Related U.S. Application Data

(62) Division of application No. 15/523,767, filed as application No. PCT/JP2015/080934 on Nov. 2, 2015, now Pat. No. 10,398,740.

(30) Foreign Application Priority Data

Nov. 4, 2014  (JP) .................................. 2014-223977

(51) Int. Cl.
*A61K 35/62* (2006.01)
*A23L 33/17* (2016.01)
*A61K 9/19* (2006.01)

(52) U.S. Cl.
CPC .............. *A61K 35/62* (2013.01); *A23L 33/17* (2016.08); *A61K 9/19* (2013.01); *A23V 2002/00* (2013.01)

(58) Field of Classification Search
None
See application file for complete search history.

(56) References Cited

U.S. PATENT DOCUMENTS

| 9,060,958 | B2 | 6/2015 | Ishii et al. |
| 9,511,098 | B2 | 12/2016 | Ishii et al. |
| 10,155,012 | B2 | 12/2018 | Ishii et al. |
| 2008/0206352 | A1 | 8/2008 | Li |
| 2009/0270465 | A1 | 10/2009 | Albright et al. |
| 2012/0294950 | A1 | 11/2012 | Ishii et al. |
| 2014/0154331 | A1 | 6/2014 | Ishii et al. |
| 2016/0317587 | A1 | 11/2016 | Ishii et al. |

FOREIGN PATENT DOCUMENTS

| CN | 103251884 | 8/2013 |
| CN | 103550537 | 2/2014 |
| EP | 0 383 533 | 8/1990 |
| JP | 57-28007 | 2/1982 |
| JP | 59-216572 | 12/1984 |
| JP | 2-215723 | 8/1990 |
| JP | 2009-508821 | 3/2009 |
| JP | 2011-522782 | 8/2011 |
| JP | 2013-32308 | 2/2013 |
| KR | 10-1198192 | 11/2012 |
| RU | 2 177 784 | 1/2002 |
| WO | 2006/082609 | 8/2006 |
| WO | 2013/018587 | 2/2013 |
| WO | 2015/108014 | 7/2015 |

OTHER PUBLICATIONS

U.S. Appl. No. 15/577,464, filed Nov. 2017, Ishii et al.
International Search Report dated Jan. 12, 2016 in International Application No. PCT/JP2015/080934.
Gloria Lee, "Tau and src family tyrosine kinases", Biochimica et Biophysica Acta (2005) 1739: 323-330.
C. Hugh Reynolds, et al., "Phosphorylation Regulates Tau Interactions with Src Homology 3 Domains of Phosphatidylinositol 3-Kinase, Phospholipase C γ1 , Grb2, and Src Family Kinases", The Journal Of Biological Chemistry (2008) 283: 18177-18186.
Takayuki Nemoto, et al., "Insulin-induced neurite-like process outgrowth: Acceleration of tau protein synthesis via a phosphoinositide 3-kinase~mammalian target of rapamycin pathway", Neurochemistry International (2011) 59: 880-888.
Gregory T. Bramblett et al., "Abnormal Tau Phosphorylation of Ser$^{396}$ in Alzheimer's Disease Recapitulates Development and Contributes to Reduced Microtubule Binding", Neuron (1993) 10: 1089-1099.
Hirotaka Yoshida, et al., "T in Paired Helical Filaments Is Functionally Distinct from Fetal T: Assembly Incompetence of Paired Helical Filament-A", J Neurochem (1993) 61: 1183-86.
Yuhao Ren et al., "Relevant activities of extracts and constituents of animals used in traditional Chinese medicine for central nervous system effects associated with Alzheimer's disease", J. Pharm. Pharmacol, 2006, 58(7), pp. 989-996.
Edwin L. Cooper et al., "Unearthing a source of medicinal molecules", Drug Discovery Today, 2010, 15 (21/22), pp. 966-972.
Extended European Search Report dated Apr. 10, 2018 in corresponding European patent application No. 15856572.1.
Akiko Yamaji et al. "Lysenin, a novel sphingomyelin-specific binding protein", Journal of Biological Chemistry, American Society for Biochemistry and Molecular Biology, US, vol. 273, No. 9, Feb. 27, 1998, pp. 5300-5306, XP002240316.

(Continued)

*Primary Examiner* — Michael Barker
(74) *Attorney, Agent, or Firm* — Wenderoth, Lind & Ponack, L.L.P.

(57) ABSTRACT

An object of the present invention is to provide: a Tau protein production accelerator containing a natural product as an active ingredient; a therapeutic or preventive agent for a disease caused by Tau protein deficiency; and a therapeutic or preventive food composition for a disease caused by Tau protein deficiency. Provided are: a Tau protein production accelerator containing a dry powder ground product and/or extract of an earthworm as an active ingredient; a therapeutic or preventive agent for a disease caused by Tau protein deficiency; and a therapeutic or preventive food composition for a disease caused by Tau protein deficiency. The disease caused by Tau protein deficiency is preferably Alzheimer's disease.

6 Claims, 4 Drawing Sheets

(56) References Cited

OTHER PUBLICATIONS

Zefeng Wang et al. "Molecular Imaging in Traditional Chinese Medicine Therapy for Neurological Diseases", BioMed Research International, 2013, XP055463571.
Office Action dated Jun. 6, 2019 in Russian Patent Application No. 2017118158, with English translation.
Search Report dated Jun. 6, 2019 in Russian Patent Application No. 2017118158, with English translation.

TAU PROTEIN PRODUCTION ACCELERATOR, AND THERAPEUTIC OR PREVENTIVE AGENT AND THERAPEUTIC OR PREVENTIVE FOOD COMPOSITION FOR DISEASES CAUSED BY TAU PROTEIN DEFICIENCY

TECHNICAL FIELD

The present invention relates to: a Tau protein production accelerator; a therapeutic or preventive agent for a disease caused by Tau protein deficiency; and a food composition for the treatment or prevention of a disease caused by Tau protein deficiency.

BACKGROUND ART

Tau proteins are a type of microtubule-associated protein. Tau proteins are particularly abundant in neurons of the central nervous system and have a function of binding to a protein called tubulin which mainly constitutes a cytoskeleton component, microtubules, and thereby stabilizing microtubules and promoting tubulin assembly into microtubules. In addition to tubulin, Tau proteins are also known to associate with other signaling molecules (Src family, PI3K, Fyn) and to promote neurite outgrowth and elongation of nerve growth cones (see, for example, Non-patent Documents 1 to 3).

Phosphorylation of Tau proteins can occur excessively in vivo. When Tau proteins are excessively phosphorylated, their binding with tubulin is inhibited, as a result of which microtubules are reduced or microtubules are destabilized and the intracellular substance transport is suppressed (see, for example, Non-patent Documents 4 and 5). Excessively phosphorylated Tau proteins aggregate with each other to form aggregates called neurofibrillary tangles. Alzheimer's disease and progressive supranuclear palsy that involve such formation of neurofibrillary tangles are classified into neurodegenerative diseases called tauopathy.

There have been proposed methods of treating a tauopathy by compensating the functions of Tau proteins. For example, U.S. Pat. No. 5,580,898 suggests the use of paclitaxel [TAXOL (registered trademark)] for the treatment of Alzheimer's disease patients through stabilization of microtubules. Further, Patent Document 1 describes an effective therapeutic method of tauopathy using a microtubule stabilizer, epothilone D.

Meanwhile, mainly in the Oriental countries, earthworm extracts and dry earthworm powders have been used since ancient times as preventive agents and therapeutic agents for various diseases, and examples of their use that have been known include bladder stone-reducing agents, bladder stone excretion-promoting agents, therapeutic agents for jaundice, oxytocics, tonic agents, hair growth agents, aphrodisiacs, antipyretics, therapeutic agents for convulsion, blood circulation promoters, therapeutic agents for hemiplegia, indirect analgesics, diuretics, antiasthmatics and antihypertensive agents.

However, no report has been made on the use of earthworms for the prevention and treatment of tauopathy such as Alzheimer's disease.

RELATED ART DOCUMENTS

Patent Document

Patent Document 1: Japanese Unexamined Patent Application Publication (Translation of PCT Application) No. 2011-522782

Non Patent Documents

Non-patent Document 1: Lee, G. Biochimica et Biophysica Acta (2005) 1739; 323-330
Non-patent Document 2: Reynolds, C H et al., THE JOURNAL OF BIOLOGICAL CHEMISTRY (2008) 283: 18177-18186
Non-patent Document 3: Nemoto, T et al., Neurochemistry international (2011) 59; 880-888
Non-patent Document 4: Bramblett G T, et al., Neuron (1993) 10: 1089-1099
Non-patent Document 5; Yoshida H, et al., J Neurochem (1993) 61: 1183-86

SUMMARY OF THE INVENTION

Problems to be Solved by the Invention

The treatment of tauopathy such as Alzheimer's disease is believed to involve drug administration over a long lime; therefore, a drug that is safe and has little side effects is particularly necessary, and there is thus a demand for a naturally derived preventive or therapeutic agent which compensates the functions of Tau protein not normally functioning due to phosphorylation.

In view of the above, an object of the present invention is to provide: a Tau protein production accelerator comprising a natural product as an active ingredient; a preventive or therapeutic agent for diseases caused by Tau protein deficiency; as well as a food composition and pharmaceutical composition for an improvement of the symptoms of diseases caused by Tau protein deficiency.

Means for Solving the Problems

That is, the Tau protein production accelerator according to the present invention is characterized by comprising a dry powder, ground product and or extract of an earthworm as an active ingredient.

The therapeutic or preventive agent for a disease caused by Tau protein deficiency according to the present invention is characterized by comprising the above-described Tau protein production accelerator.

The therapeutic or preventive food composition for a disease caused by Tau protein deficiency according to the present invention is characterized by comprising the above-described Tau protein production accelerator.

In the therapeutic or preventive agent for a disease caused by Tau protein deficiency according to the present invention, it is preferred that the disease caused by Tau protein deficiency be Alzheimer's disease.

In the therapeutic or preventive food composition for a disease caused by Tau protein deficiency according to the present invention, it is preferred that the disease caused by Tau protein deficiency be Alzheimer's disease.

The method of producing a Tau protein production accelerator according to the present invention is characterized by comprising the use of a dry powder, ground product or extract of an earthworm.

The method of producing a therapeutic or preventive agent for a disease caused by Tau protein deficiency according to the present invention is characterized by comprising the use of a dry powder, ground product or extract of an earthworm.

The method of producing a therapeutic or preventive food composition for a disease caused by Tau protein deficiency according to the present invention is characterized by comprising the use of a dry powder, ground product or extract of an earthworm The method of promoting Tau protein production according to the present invention is characterized by comprising the use of a dry powder, ground product and or extract of an earthworm.

The dry powder, ground product or extract of an earthworm according to the present invention is for the use in the treatment of a disease caused by Tau protein deficiency.

The method of treating or preventing a disease caused by Tau protein deficiency according to the present invention is characterized by comprising administration of a dry powder, ground product and/or extract of an earthworm to a subject in an effective dose.

Effects of the Invention

According to the present invention, a Tau protein production accelerator comprising a natural product as an active ingredient, a preventive or therapeutic agent for diseases caused by Tau protein deficiency, as well as a food composition and pharmaceutical composition for an improvement of the symptoms of diseases caused by Tau protein deficiency can be provided.

BRIEF DESCRIPTION OF THE DRAWINGS

FIG. 2A shows, from the left, the pTau concentration and the Tau protein concentration, both of which are based on β-actin, as well as the ratio of pTau with respect to Tau protein; FIG. 2B shows, from the left, the pAkt concentration and the Akt concentration, both of which are based on β-actin, as well as the ratio of pAkt with respect to Akt; and FIG. 2C shows, from the left, the pGSK-3β concentration and the GSK-3β concentration, both of which are based on β-actin, as well as the ratio of pGSK-3β with respect to GSK-3β.

FIG. 3A provides photographs showing the results of Western blotting which was performed to investigate the changes in the amounts of Tau protein (Tau) and β-actin produced in rat hippocampal neurons during culture in a dry earthworm powder-dissolved culture medium (48 hours, 37° C.) in accordance with changes in the concentration of dissolved dry earthworm powder; and FIG. 3B is a graph showing the changes in the concentration of Tau protein based on β-actin, which were quantified using an image analysis software ImageJ64.

FIG. 4A provides photographs showing the results of Western blotting which was performed to investigate the changes in the amounts of Tau protein (Tau) and β-actin produced in rat hippocampal neurons during culture in a dry earthworm powder-dissolved culture medium (37° C., concentration of dissolved dry earthworm powder: 100 ng/ml) in accordance with changes in the duration of culture period; and FIG. 4B is a graph showing the changes in the concentration of Tau protein based on β-actin, which were quantified using an image analysis software ImageJ64.

FIG. 5 shows immunostained fluorescence images of Tau protein (Tau) and pTau in rat hippocampal neurons that were cultured at 37° C. for 48 hours in a culture medium NM5 or a culture medium prepared by dissolving dry earthworm powder in a culture medium NM5 (100 ng/ml). The upper row (None) shows the fluorescence images obtained for the rat hippocampal neurons in the culture medium, while the lower row (RW) shows the fluorescence images obtained for the rai hippocampal neurons in the dry earthworm powder-dissolved culture medium. The left column shows the fluorescence images of Tau protein; the center column shows the fluorescence images of pTau; and the right column shows the fluorescence images of Tau protein and pTau.

MODE FOR CARRYING OUT THE INVENTION

Figure 1:
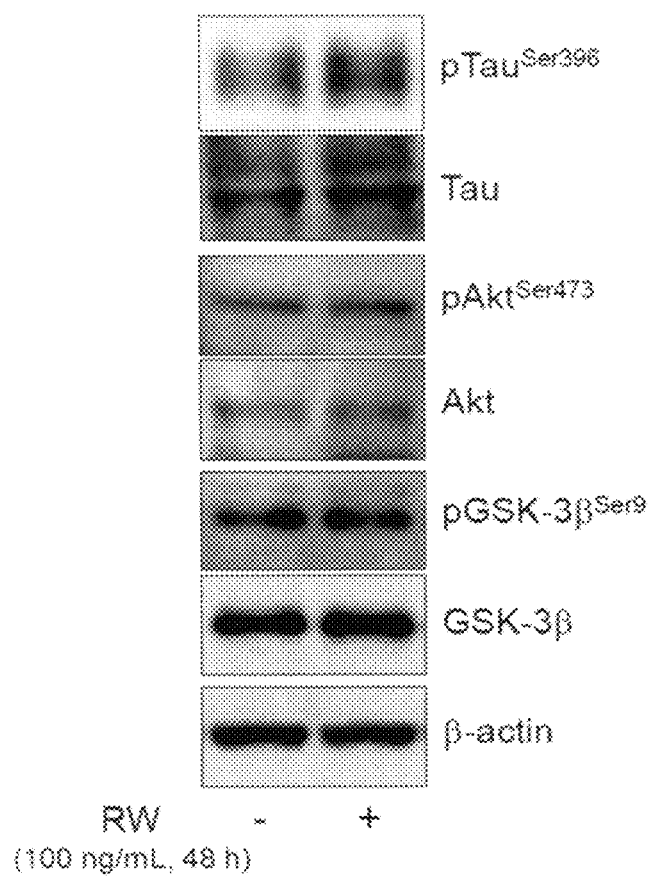
FIG. 1 provides photographs showing the results of Western blotting which was performed to investigate the changes in the amounts of Tau protein (Tau), Akt, GSK-3β and β-actin produced in rat hippocampal neurons during culture in a dry earthworm powder-dissolved culture medium (48 hours, 37° C., concentration of dissolved dry earthworm powder: 100 ng/ml) as well as the changes in the amounts of phosphorylated Tau protein (Tau), Akt and GSK-3β (pTau, pAkt and pGSK-3β, respectively). The "−" and "+" columns show the results of culturing rat hippocampal neurons in a culture medium NM5 and a culture medium prepared by dissolving dry earthworm powder in a culture medium NM5 (100 ng/ml), respectively. It is noted here that Tau protein, Akt and GSK-3β were evaluated using Ser396, Ser473 and Ser9 as an index of phosphorylation, respectively.

In the method of the present invention, the earthworm used as a raw material is not particularly restricted, and examples of earthworms that can be used include *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldt* Horst, *Pheretima hilgendorfi, Pontodrilus matsushimensis* Iizuka, *Tubifex hattai* Nomura, and *Limnodrilus gotoi* Hatai (=*L. socialis* Stephenson).

In the present invention, the term "dry powder" of an earthworm means powder obtained by drying a ground product or extract of an untreated or pretreated earthworm. The term "ground product" of an earthworm means an untreated or pretreated earthworm ground into a liquid or paste form. The term "extract" of an earthworm means an extract obtained by dissolving an untreated or pretreated earthworm or a ground product thereof in water or an organic solvent and subsequently removing or separating insoluble fractions. The pretreatment is not particularly restricted, and examples thereof include the below-described treatment for removal of dirt and the like. Further, the dry powder, ground product and extract of an earthworm may also be subjected to a post-treatment, examples of which include granulation, filtration, purification, concentration, dilution and pH adjustment.

The grinding method for obtaining a ground product of an earthworm is not particularly restricted, and grinding can be performed by using, for example, a homogenizer, a blender, a homomixer, a grinder or a high-pressure cell crushing apparatus.

The extraction method for obtaining an extract of an earthworm is not particularly restricted and extraction can be performed by, for example, dissolving dry powder or a ground product of the earthworm in an extraction solvent and subsequently removing or separating insoluble fractions. Examples of the extraction solvent include water, aqueous solutions, and organic solvents such as ethanol, acetone and ethyl acetate, and these extraction solvents may be used individually, or two or more thereof may be used in combination. Thereamong, water, ethanol or an aqueous ethanol solution is preferably used.

The drying method for obtaining a dried product of an earthworm is not particularly restricted, and drying can be performed by a drying method such as freeze-drying, heat-drying or spray-drying. Thereamong, freeze-drying is preferred for the below-described reasons.

In the present invention, the dry powder, ground product or extract of the earthworm can be incorporated in an effective amount in accordance with the purpose thereof. The appropriate amount depends on a variety of factors such as the intended purpose, the route and mode of administration and the production method of the dry powder or the like of the earthworm; however, for the purpose of preventing diseases caused by Tau protein deficiency or treating a mild disease, the appropriate amount is preferably 1 to 15,000 mg/day, more preferably 12 to 1,800 mg/day, still more preferably 120 to 180 mg/day, in terms of the weight of the dry powder of the earthworm obtained by removing the digested matters remaining in the digestive tract of the earthworm as well as the dirt and the like adhering to the skin of the earthworm as described below, grinding the earthworm and then freeze-drying the resulting ground product. Further, for the purpose of treating a severe disease caused by Tau protein deficiency, the appropriate amount is preferably 1 to 15,000 mg/day, more preferably 18 to 3,600 mg/day, still more preferably 180 to 360 mg/day.

The forms of the Tau protein production accelerator, therapeutic agent, preventive agent and food composition of the present invention are not particularly restricted and can be any of a solid form, a powder form, a semisolid form and a liquid form.

In the present invention, the dry powder, ground product or extract of the earthworm can be used as is. Alternatively, particularly the Tau protein production accelerator, therapeutic agent and preventive agent of the present invention may contain a pharmaceutically acceptable carrier and can be administered orally or parenterally (e.g., intravenous administration or direct administration to the affected site) in the form of a tablet, a granule, a powder, a capsule, a soft capsule, a liquid, an injectable, a suppository or a sustained release agent or the like. As the pharmaceutically acceptable carrier, for example, an excipient, a binding agent, a disintegrant, a fluidizing agent, a lubricant, a coating agent, a suspending agent, a colorant, a sweetening agent or a surfactant can be used, and the resultant can be made into the form of an ordinary pharmaceutical preparation in accordance with a known method. Further, other therapeutic and preventive components) and pharmaceutically acceptable additive(s) may also be incorporated.

In the present invention, particularly in the Tau protein production accelerator and food composition of the present invention, an additive(s) usually used in food products may also be incorporated. Examples of additives that can be used include an excipient, a binding agent, a disintegrant, a fluidizing agent, a lubricant, a coating agent, a suspending agent, a colorant, a sweetening agent and a surfactant, and the resultant can be made into the form of an ordinary food composition in accordance with a known method. Further, other food product(s) or food-derived components) may be incorporated as well.

In the present invention, among a dry powder, a ground product and an extract of earthworms, from the standpoint of the storage stability in the production process, it is preferred to use a dry powder of an earthworm. The dry powder of an earthworm may be dissolved and/or dispersed in a liquid such as water in advance and the resultant may be subsequently mixed with other components), examples of which include conventional carriers and additives that are used pharmaceutically and/or in food products.

In the present invention, the disease caused by Tau protein deficiency is not particularly restricted; however, it is preferably a tauopathy, more preferably one selected from the group consisting of Alzheimer's disease, Pick's disease, corticobasal degeneration, progressive supranuclear palsy, chronic traumatic encephalopathy, frontotemporal dementia and parkinsonism linked to chromosome 17, Parkinsonism-dementia complex of Guam, neurofibrillary tangle-predominant senile dementia accompanied by neurofibrillary tangles similar to those of amyloid plaque-free Alzheimer's disease, ganglioglioma, gangliocytoma, subacute sclerosing panencephalitis, tuberous sclerosis, Hallervorden-Spatz disease, frontotemporal dementia, and frontotemporal lobar degeneration. The disease caused by Tau protein deficiency is particularly preferably Alzheimer's disease.

For oral administration of an earthworm as a raw material, it is preferred to remove the digested matters remaining in the digestive tract of the earthworm, the dirt adhering to the skin and the like. In the present invention, the method for such removal is not particularly restricted, and the removal can be performed by a known method. For example, a method of allowing a live earthworm to excrete yellow soil contained in the digestive tract by immersing the earthworm into an aqueous solution of an alkali salt such as a sodium salt or a potassium salt (method described in Japanese Unexamined Patent Application Publication Nos. H1-47718, H1-47719, H1-47720 and H1-268639) or a method of removing castings from the digestive tract of a five earthworm by leaving the earthworm in an aqueous acid solution maintained at 6 to 26° C. for 0.1 to 5 hours (method described in Japanese Unexamined Patent Application Publication No. H3-72427) can be employed.

In the present invention, as a removal method, it is preferred to bring the earthworm into contact with the below-described metal chloride and/or hydroxycarboxylic acid.

The metal chloride is a chloride of at least one metal selected from the group consisting of potassium, sodium, magnesium and calcium. That is, the metal chloride is at least one selected from the group consisting of potassium chloride, sodium chloride, magnesium chloride and calcium chloride. Further, the metal chloride may also be a mixture of these metal chlorides, or a mixture of one or more of these metal chlorides and other harmless component(s) that can be added to food products. Examples of such mixtures include dietary salts, rock salts and bay salts. The metal chloride can be used by sprinkling it in a powder form over a live earthworm, and this causes a contact between the earthworm and the metal chloride.

After allowing the metal chloride to come into contact with the live earthworm, it is preferred to bring the live earthworm into contact with a hydroxycarboxylic acid in the below-described manner. Alternatively, the earthworm may be brought into contact with a hydroxycarboxylic acid in the below-described manner without a preceding contact with the metal chloride.

The contact with the hydroxycarboxylic acid can also be made by sprinkling the hydroxycarboxylic acid in a powder form over the live earthworm. Alternatively, the live earthworm may be immersed in an aqueous solution of the hydroxycarboxylic acid that has a pH of 2 to 5. In cases where the contact with the hydroxycarboxylic acid is made after a contact with the metal chloride, it is preferred that the contact with the hydroxycarboxylic acid be made promptly after the contact with the metal chloride. It is also preferred that the earthworm be washed with water before being brought into contact with the hydroxycarboxylic acid. By removing the metal chloride by washing with water and then bringing the earthworm into contact with the hydroxycarboxylic acid, a dry earthworm powder having a high enzyme activity can be obtained. When the earthworm is washed with water before the contact with the hydroxycarboxylic acid, the washing of the earthworm with water is performed preferably within 30 minutes, more preferably within 20 minutes, after the initiation of the contact with the metal chloride. The method of washing the earthworm with water is not particularly restricted, and a known method can be employed.

If live earthworms are left in contact with hydroxycarboxylic acid powder for a long time, the earthworms are killed, so that their vital functions are lost and the digested matters in their digestive tracts are no longer excreted. Therefore, it is preferred to dilute the hydroxycarboxylic acid with water as soon as possible, preferably within 30 seconds, more preferably within 20 seconds, so as to adjust the pH to a range of 2 to 5.

Since a hydroxycarboxylic acid creates a living environment unpleasant to earthworms, live earthworms, following their self-preservation instinct, try to improve the living environment through discharge of body fluids and excretion. Further, since hydroxycarboxylic acids have disinfecting properties, they are expected not only to play a role in promoting excretion of digested mailers and the like remaining in the digestive tract as described above, but also to have an effect of killing bacteria adhering to earthworms.

In the above-described method, any crystalline hydroxycarboxylic acid can be used regardless of the number of its hydroxy groups and carboxyl groups, as long as it assumes a crystalline form under the conditions of its use. That is, the crystalline hydroxycarboxylic acid may be any of monohydroxy monocarboxylic acids, monohydroxy polycarboxylic acids, polyhydroxy monocarboxylic acids and polyhydroxy polycarboxylic acids.

Examples of the hydroxycarboxylic acid used in the present invention include glycolic acid, lactic acid, acetic acid, β-hydroxypropionic acid, α-hydroxy-n-butyric acid, β-hydroxy-n-butyric acid, α-hydroxy-n-valeric acid, β-hydroxy-n-valeric acid, malic acid, α-methylmalic acid, α-hydroxyglutaric acid, β-hydroxyglutaric acid, citric acid, malonic acid and succinic acid. Thereamong, lactic acid, acetic acid, malic acid, citric acid, malonic acid and succinic acid are preferred because they can be used in food products and easily obtained. The above-described hydroxycarboxylic acids may be used individually, or two or more thereof may be used in combination.

Water constitutes 65% of the tissues of a live earthworm. Although the self-preservation functions of a live earthworm remain effective for a certain lime, the death of the live earthworm results in the onset of enzyme activities; therefore, it is required to carefully control the period of placing the live earthworm under an unpleasant living environment. The duration of this period varies depending on the conditions; however, it is usually in a range of 3 to 180 minutes.

It is preferred that the thus hydroxycarboxylic acid-treated five earthworm be washed with water and then ground into a liquid-form or paste-form ground product. The washing is preferably performed with pure water. The washing method is not particularly restricted, and a known washing method with water can be employed. The total time of the treatment process before the grinding, that is, the duration of the period from the sprinkling of the metal chloride on the live earthworm to the completion of the removal of the hydroxycarboxylic acid by washing with water, is preferably not longer man 240 minutes.

The grinding method is not particularly restricted and, for example, the grinding is usually performed at 1 to 25° C. by using a homogenizer, a blender, a homomixer, a grinder, a high-pressure cell-crushing apparatus or the like. From the standpoint of inhibiting degradation of the earthworm components, it is preferred that the grinding be performed at a low temperature, more preferably at a temperature of 2 to 15° C.

The ground product obtained by grinding the earthworm is placed on a stainless-steel tray or the like and subjected to freeze-drying. In this process, a decomposition gas may be generated because the enzymes contained in the living body of the earthworm are inactive in the living cells but act instantaneously on dead cells. In order to inhibit the generation of a decomposition gas, it is preferred that, before being freeze-dried, the ground product be momentarily cooled rapidly and frozen at −18° C. to −35° C. so as to suppress the enzyme actions.

In this manner, for the preparation of earthworm powder without impairing the inherent pharmacological actions of the earthworm, it is preferred that the ground earthworm be quickly frozen. On the other hand, an excessively rapid freezing is not preferred because when the ground earthworm is frozen in an excessively short period of time, the impurities existing together with the proteins that are major components of an earthworm paste can form spots of unfrozen pans and thus may not be separated. Therefore, the freezing is performed at a low temperature of −18° C. to −35° C. over a period of preferably 20 to 240 hours, more preferably 50 to 170 hours.

For the freeze-drying, it is important to select conditions that allow removal of water as well as impurities without leaving any impurity. Accordingly, it is preferred that the freeze-drying be per formed under a pressure of 50 Pa or less while increasing the temperature stepwise in a range of −60° C. to +90° C. over a period of 10 to 60 hours.

As a freeze-drying method, for example, as described above, after freezing the ground product at a temperature of −18° C. to −35° C. over a period of 20 to 240 hours, the resultant is vacuum freeze-dried over a period of 10 to 60 hours while increasing the temperature in several steps in a range of −60° C. to +90° C. and reducing the pressure in several steps in a range of 25 to 40 Pa, whereby a sterile pale yellow dry earthworm powder can be obtained.

Further, it is also preferred to incorporate the steps of dissolving the thus freeze-dried ground product in water or an aqueous ethanol solution; and removing or separating insoluble fractions. The step of removing or separating insoluble tractions can be performed in the same manner as described above and comprises precipitation carried out by leaving the resulting solution to stand, centrifugation, filtration and the like. The step of dissolving the freeze-dried ground product in water or an aqueous ethanol solution is preferably performed with stirring or shaking. The time required for dissolution of the freeze-dried ground product in water is preferably 1 to 120 minutes, more preferably 5 to 80 minutes. The ethanol concentration of the aqueous ethanol solution is not particularly restricted; however, it is preferably 10 to 70% (v/v), more preferably 30 to 60%.

As the Tau protein production accelerator, therapeutic agent, preventive agent and food composition of the present invention, a supernatant obtained from water or aqueous ethanol solution in which freeze-dried ground earthworm is dissolved as described above may be used as it is in the state of an aqueous solution, or may be used in the form of a concentrate after evaporating water therefrom. The supernatant may also be dried to be used in a powder form, and the powder obtained by drying the supernatant may be dissolved in water for use. Further, powder obtained by freeze-drying an earthworm paste can be used as it is, without being dissolved in water or an aqueous ethanol solution.

In the present invention, as a removal method, before the treatment of placing live earthworms under an unpleasant environment, that is, before bringing live earthworms into contact with a metal chloride or a hydroxycarboxylic acid as described above, it is preferred that the live earthworms be transferred to a flat box such as a bread box and left to stand for 10 to 50 hours in a bright place, followed by removal of dirt adhering to the earthworm skin. The duration of leaving the live earthworms in a bright place is more preferably 12 to 24 hours. In this process, it is preferred that the amount of the live earthworms contained in the flat box be such an amount that the earthworms are piled up to a thickness of 30 to 60 mm, preferably 40 to 50 mm. Care should be taken so that the flat box contains no foreign matter such as sand or mud and, since earthworms are nocturnal and thus become active in their living activities in dark place and this may lead to their physical exhaustion, it is preferred to employ a light culture method or the like during the night so as to keep the flat box under a bright condition. This treatment makes the live earthworms exhibit their self-protection instinct and try to maintain their living environment by excreting the digested matters remaining in their digestive tracts, covering their entire body with the excrements and thereby preventing evaporation of water. Thus, by repeatedly striping off this covering dirt, namely excrements, by an appropriate means, the digested matters in the digestive tracts of the earthworms and the dirt adhering to their skin can be eventually removed.

The dirt adhering to the earthworms' skin can be stripped off by, for example, covering the live earthworms with a nonwoven fabric and allowing the dirt to adsorb to the fabric. By performing this process of leaving the earthworms in a bright place and removing the dirt adhering to their skin in combination with the above-described process of bringing the earthworms into contact with the a metal chloride and/or a hydroxycarboxylic acid, further excretion and removal of toxic matters contained in the earthworms' body can be expected.

In the present invention, as a method for obtaining a dry earthworm powder, the following methods are preferred particularly from the standpoint of the storage stability of the resulting dry powder.

(A-1) A method of producing a dry earthworm powder, the method comprising the steps of:

bringing a live earthworm into contact with a chloride of at least one metal selected from the group consisting of potassium, sodium, magnesium and calcium; and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water, grinding the live earthworm and then freeze-drying the thus obtained ground product.

(A-2) A method of producing a dry earthworm powder, the method comprising the steps of:

bringing a live earthworm into contact with a chloride of at least one metal selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm and then freeze-drying the thus obtained ground product.

(A-3) The method of producing a dry earthworm powder according to the above-described (A-1) or (A-2), which further comprises the steps of: dissolving the thus freeze-dried ground product into water or an aqueous ethanol solution; removing or separating insoluble fractions; and then further freeze-drying the resultant.

Further, after the freeze-drying of the ground product obtained by grinding the live earthworm, from the standpoint of sterilization of the resulting dried product, the dried product is preferably heat-treated at a temperature of 110° C. or higher but lower than 130° C. When the heating temperature is lower than 110° C., the dried product may not be sterilized sufficiently, whereas when the heating temperature is 130° C. or higher, the enzymes contained in the dried earthworm product are inactivated and their activities are thus reduced, which is not preferred. The healing temperature is more preferably 115 to 125° C. The heating method is not particularly restricted, and examples thereof include a method of blowing hot air; a method using a healing jacket; a method of heating the subject on a tray or the like using a heater; and a method using a thermostat incubator. The heating time is preferably 30 seconds to 130 minutes, more preferably 30 minutes to 90 minutes, still more preferably 60 minutes to 90 minutes. An excessively short heating time may result in insufficient sterilization while an excessively long heating time may cause the loss of enzyme activities, neither of which is preferred. When enzymes contained in a liquid are subjected to the above-described heat treatment, the activities of the enzymes are lost; therefore, in the present invention, it is preferred to use a dry earthworm powder.

In the present invention, as a method for obtaining a ground product of an earthworm, the following methods are preferred.

(B-1) A method of producing a ground product of an earthworm, the method comprising the steps of:

bringing a live earthworm into contact with a chloride of at least one metal selected from the group consisting of potassium, sodium, magnesium and calcium: and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water and then grinding the live earthworm.

(B-2) A method of producing a ground product of an earthworm, the method comprising the steps of:

bringing a live earthworm into contact with a chloride(s) of a metal(s) selected from the group consisting of potassium, sodium, magnesium and calcium, and subsequently immersing and maintaining the live earthworm for 3 to 180 minutes in an aqueous hydroxycarboxylic acid solution having an adjusted pH of 2 to 5, washing the live earthworm with water and then grinding the live earthworm.

In the present invention, as a method for obtaining an earthworm extract, the following methods are preferred.

(C-1) A method of producing an earthworm extract, the method comprising the steps of:

bringing a live earthworm into contact with a chloride of at least one metal selected from the group consisting of potassium, sodium, magnesium and calcium; and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water, grinding the live earthworm, freeze-drying the resulting ground product, dissolving the thus freeze-dried product in water or an aqueous ethanol solution, and then removing or separating insoluble fractions.

(C-2) A method of producing an earthworm extract, the method comprising the steps of:

bringing a live earthworm into contact with a chloride(s) of a metal(s) selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm, freeze-drying the resulting ground product, dissolving the thus freeze-dried product in water or an aqueous ethanol solution, and then removing or separating insoluble fractions.

Examples

The present invention will now be described in more detail by way of examples thereof. The present invention, however, is not restricted by the following examples by any means. It is noted here that, unless otherwise specified, "%" used below is all based on mass.

[Preparation of Dry Earthworm Powder]

After leaving 30 kg of live red earthworms (*Lumbricus rubellus*) to stand in a bright place for 24 hours and stripping off dirt adhering to their skin, the live red earthworms were spread at a thickness of about 5 cm on a flat dish, and 250 g of sodium chloride was uniformly sprinkled thereon. The earthworms were washed with water 20 minutes thereafter. Then, 15 seconds after sprinkling 250 g of citric acid on the earthworms in the same manner, 30 L of pure water was added thereto for dilution. In this process, the pH of the resulting solution was 2.25 immediately after the addition of water and 2.74 after the completion of the dilution. When sprinkled with the citric acid powder, the earthworms excreted yellow body fluid at once. After the dilution with water, the earthworms were maintained in this state for 20 minutes. Next, the live earthworms were taken out of the resulting dirty aqueous citric acid solution, washed with water and subsequently ground at 10° C. using a homogenizer to prepare an earthworm paste. Then, after subjecting this earthworm paste to vacuum degassing so as to remove the gases contained therein, the earthworm paste was transferred to a stainless-steel tray where the earthworm paste was instantaneously and rapidly cooled to −35° C. and maintained at this temperature for 50 hours to be slowly frozen. The thus frozen earthworm paste was maintained at −35° C. under a pressure of 0 Pa for 2 hours. Thereafter, the earthworm paste was heated and dried at 25° C. under a pressure of 40 Pa for 10 hours, at 40° C. under a pressure of 35 Pa for 14 hours and then at 65° C. and a pressure of 35 Pa for 12 hours and lastly, the resultant was maintained at a temperature of 80° C. and a pressure of 25 Pa for 6 hours, thereby vacuum freeze-drying the earthworm paste. By this treatment, a pale-yellow dry earthworm powder having a water content of 8% by mass was obtained.

The thus obtained dry earthworm powder was heat-treated using a heating apparatus RM-50D (manufactured by Okawara MFG. CO., Ltd.). As for the heating conditions, the dry earthworm powder was heated to 120° C. over a period of 90 minutes, maintained at 120° C. for 20 minutes and then cooled to 40° C. over a period of 240 minutes. Thereafter, the dry earthworm powder was taken out.

The thus heat-treated dry earthworm powder was dissolved in 50% aqueous ethanol solution such that a ratio, ethanol:freeze-dried powder, of 20:1 (v/w) was attained, and the resulting solution was shaken for 1 hour at 1,500 rpm under room temperature (25° C.). Then, the solution was centrifuged for 15 minutes at 4° C. and 10,000×g, and the resulting supernatant was separated and vacuum-concentrated at 75° C. for 15 minutes. This supernatant was transferred to a stainless-steel tray where the supernatant was instantaneously and rapidly cooled to −35° C. and maintained at this temperature for 50 hours to be slowly frozen. The thus frozen earthworm paste was maintained at −35° C. under a pressure of 0 Pa for 2 hours. Thereafter, the earthworm paste was heated and dried at 25° C. under a pressure of 40 Pa for 10 hours, at 40° C. under a pressure of 35 Pa for 14 hours and then at 65° C. under a pressure of 35 Pa for 12 hours and lastly, the resultant was maintained at a temperature of 80° C. and a pressure of 25 Pa for 6 hours, thereby vacuum freeze-drying the earthworm paste to obtain a dry earthworm powder A-1.

[Rat Hippocampal Neuron Culture]

Nerve cells (neurons) isolated from the hippocampal region of a rat embryo at day 18 of gestation were cultured at 37° C. for 7 days.

[Quantification of Tau Protein and Phosphorylated Tau Protein]

The thus cultured rat hippocampal neurons were cultured at 37° C. in 1 ml of freeze-dried earthworm powder-dissolved culture media each prepared by dissolving the above-obtained dry earthworm powder A-1 in a culture medium, Neural Media 5 (NM5), at a concentration of 0, 1, 10, 100 or 1,000 ng/mL (cell number: $1\times10^6/12$ well dish). The formulation of the culture medium NM5 is as follows:

230 mL of Neurobasal (Gibco 21103-049)

12.5 mL of horse serum (Sigma H1270)

2.5 mL of penicillin/streptomycin (Gibco 15140122)

5 mL of Glutamax 1 (Gibco 35050-061)

2% B27 supplement (Gibco 17504044)

Subsequently, after an arbitrary time period, the rat hippocampal neurons were recovered, washed twice with PBS (−) solution and then adjusted with a sample buffer, and the amount of Tau protein and that of phosphorylated Tau protein were evaluated by Western blotting. The protein amount and phosphorylation amount were determined using an image analysis software, ImageJ64, based on the results of Western blotting. The protein amount and phosphorylation amount were also evaluated in the same manner for Akt and GSK-3β molecules positioned in the signaling upstream of Tau protein.

Figure 2A:
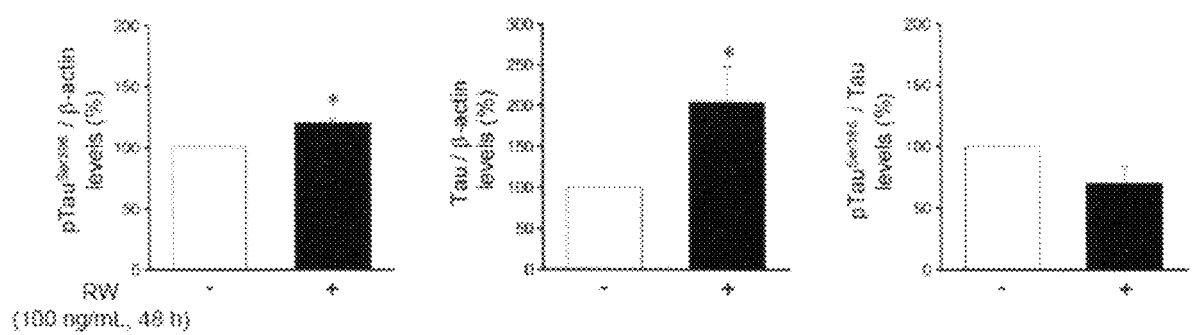
FIGS. 2A-2C provide graphs showing the concentrations of Tau protein (Tau), Akt and GSK-3β as well as the concentrations of phosphorylated Tau protein (pTau), Akt (pAkt) and GSK-3β (pGSK-3β), which were quantified from the results of Western blotting shown in FIG. 1 using an image analysis software ImageJ64.
Figure 2B:
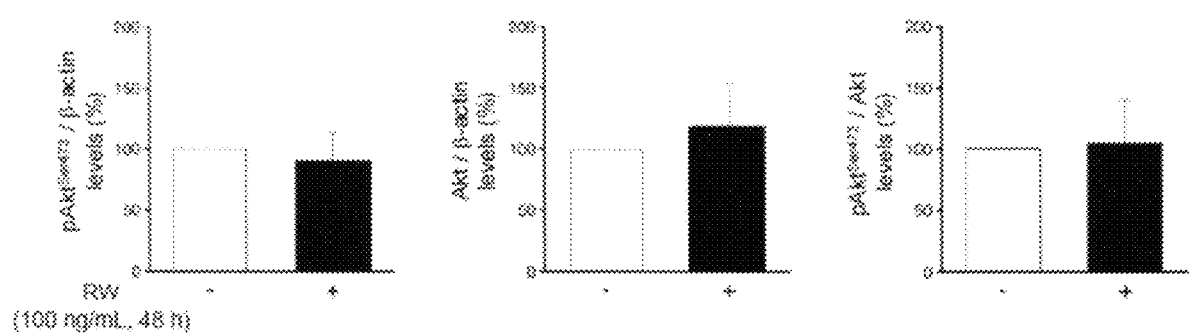
Figure 2C:
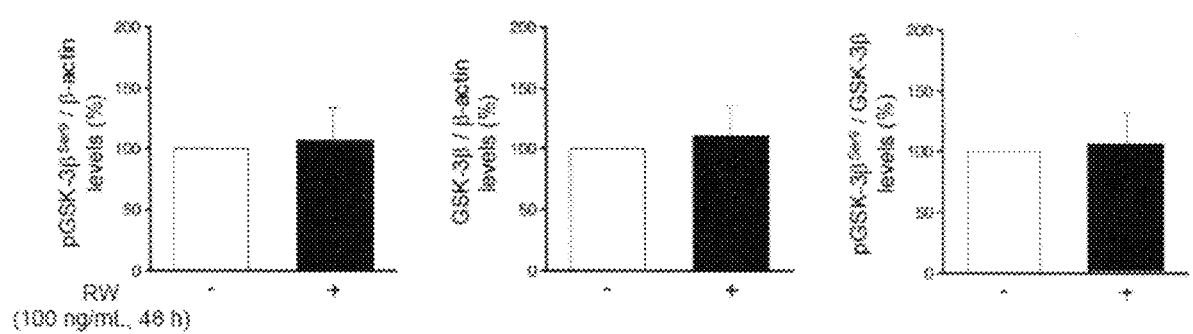

In the rat hippocampal neurons that were cultured in the dry earthworm powder-dissolved culture media, no significant increase in the protein amount was found for AKt and GSK-3β (FIGS. 1, 2B and 2C); however, it was found that the amount of Tau protein was increased and that the protein was produced in more than double the amount as compared to the control ("–"; cultured in a culture medium NM5) (FIGS. 1 and 2A). In addition, with regard to the increase in the amount of Tau protein attained by the use of the dry earthworm powder-dissolved culture media, the maximum increase was found at a dry earthworm powder concentration of 100 ng/mL and a culture time of 48 hours (FIGS. 3 and 4).

[Intracellular Localization of Tau Protein and Phosphorylated Tau Protein]

The above-cultured rat hippocampal neurons were cultured at 37° C. in 2 ml of a solution prepared by dissolving the above-obtained dry earthworm powder A-1 in a culture medium NM5 at a concentration of 100 ng/mL (cell number: $2 \times 10^5$/6 well dish (with a cover glass on the bottom)).

Then, after 48 hours, the rat hippocampal neurons were recovered and fixed with 4% paraformaldehyde, and intracellular localization was examined for Tau protein and phosphorylated Tau protein by immunostaining.

In the control ("None"; cultured in a culture medium NM5), even the neurites were clearly observed with phosphorylation of Tau protein; however, in the hippocampal neurons cultured in the dry earthworm powder-dissolved culture medium, no clear image of phosphorylation was confirmed at the neurites (FIG. 5).

From the above results, it is seen that dry earthworm powder not only significantly increases the amount of Tau protein but also reduces the amount of phosphorylation especially at the neurites.

The invention claimed is:

1. A method of promoting Tau protein production, said method comprising administration of a Tau protein production accelerator comprising a dry powder, ground product and/or extract of an earthworm to a subject in an effective dose, wherein the dry powder, ground product and/or extract of an earthworm is prepared by a method comprising the steps of: bringing a live earthworm into contact with a chloride of at least one metal selected from the group consisting of potassium, sodium, magnesium and calcium; and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water, grinding the live earthworm and then freeze-drying the thus obtained ground product.

2. A method of promoting Tau protein production, said method comprising administration of a Tau protein production accelerator comprising a dry powder, ground product and/or extract of an earthworm to a subject in an effective dose, wherein the dry powder, ground product and/or extract of an earthworm is prepared by a method comprising the steps of: bringing a live earthworm into contact with a chloride of at least one metal selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm and then freeze-drying the thus obtained ground product.

3. A method of treating or preventing a disease caused by Tau protein deficiency, said method comprising administration of a dry powder, ground product and/or extract of an earthworm to a subject in an effective dose, wherein the dry powder, ground product and/or extract of an earthworm is prepared by a method comprising the steps of: bringing a live earthworm into contact with a chloride of at least one metal selected from the group consisting of potassium, sodium, magnesium and calcium; and subsequently bringing the live earthworm into contact with a powder-form hydroxycarboxylic acid, diluting the resultant with water to adjust the pH to 2 to 5, maintaining the resulting dilution for 3 to 180 minutes, washing the live earthworm with water, grinding the live earthworm and then freeze-drying the thus obtained ground product.

4. The method according to claim 3, wherein said disease caused by Tau protein deficiency is Alzheimer's disease.

5. A method of treating or preventing a disease caused by Tau protein deficiency, said method comprising administration of a dry powder, ground product and/or extract of an earthworm to a subject in an effective dose, wherein the dry powder, ground product and/or extract of an earthworm is prepared by a method comprising the steps of: bringing a live earthworm into contact with a chloride of at least one metal selected from the group consisting of potassium, sodium, magnesium and calcium; and subsequently immersing and maintaining the live earthworm for 3 to 180 minutes in an aqueous hydroxycarboxylic acid solution having an adjusted pH of 2 to 5, washing the live earthworm with water, grinding the live earthworm and then freeze-drying the thus obtained ground product.

6. The method according to claim 5, wherein said disease caused by Tau protein deficiency is Alzheimer's disease.

* * * * *